United States Patent [19]

Kruse et al.

[11] Patent Number: 4,968,848

[45] Date of Patent: Nov. 6, 1990

[54] PROCESS OF THE PRPARATION OF PERFLUOROALKYL COMPOUNDS, AND PENTAFLUOROETHYLTRIMETHYLSILANE

[75] Inventors: Alfred Kruse, Kelkheim; Günter Siegemund, Hofheim am Taunus; Axel Schumann, Alfter, all of Fed. Rep. of Germany

[73] Assignee: Hoechst Aktiengesellschaft, Frankfurt am Main, Fed. Rep. of Germany

[21] Appl. No.: 313,375

[22] Filed: Feb. 21, 1989

[30] Foreign Application Priority Data

Feb. 23, 1988 [DE] Fed. Rep. of Germany ....... 3805534

[51] Int. Cl.$^5$ ..................... C07C 33/46; C07C 35/20; C07C 35/08; C07C 35/06
[52] U.S. Cl. ..................... 568/812; 568/821; 568/822; 568/828; 568/832; 568/838; 568/839; 568/842; 568/843; 556/470; 556/482; 556/485
[58] Field of Search ............... 568/812, 821, 822, 832, 568/828, 838, 839, 842, 843; 556/470, 482, 485

[56] References Cited

U.S. PATENT DOCUMENTS

| | | | |
|---|---|---|---|
| 3,536,745 | 10/1970 | Dear | 556/470 |
| 4,383,120 | 5/1983 | Yates | 556/470 |
| 4,430,504 | 2/1984 | Reuter et al. | 556/482 |
| 4,613,681 | 9/1986 | Foulletier et al. | 568/842 X |
| 4,780,554 | 10/1988 | Quirk et al. | 556/482 X |
| 4,785,126 | 11/1988 | Bruno | 556/470 X |

OTHER PUBLICATIONS

Tetrahedron Letters 25, 2195–8 (1984).

Primary Examiner—Paul F. Shaver

[57] ABSTRACT

A process for the preparation of perfluoroalkyl compounds which comprises reacting a perfluoroalkyltrimethylsilane of the general formula $(CH_3)_3Si-C_nF_{2n+1}$ (I), wherein the group $C_nF_{2n+1}$ represents a perfluoroalkyl group having from 1 to 6 carbon atoms, with a carbonyl compound of the general formula $R^1-CO-R^2$ (II), wherein $R^1$ represents a hydrocarbon group or hydrogen and $R^2$ represents a hydrocarbon group, a perfluoroalkyl group or a perfluoroaryl group, but wherein $R^1$ and $R^2$ together may also be part of an alicyclic ring system, in the presence of a salt-like fluoride—which is at least partially soluble in the reaction medium—as a catalyst to yield a silylether of the formula

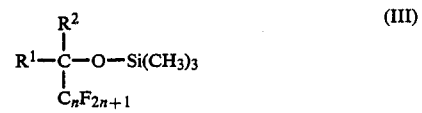

and isolating this compound or hydrolyzing it to yield an alcohol of the formula IV

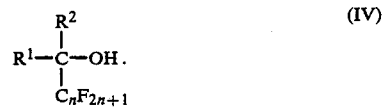

The invention also relates to pentafluoroethyl trimethylsilane $(CH_3)_3Si-CF_2CF_3$ and a process for the preparation of this compound.

13 Claims, No Drawings

PROCESS OF THE PRPARATION OF PERFLUOROALKYL COMPOUNDS, AND PENTAFLUOROETHYLTRIMETHYLSILANE

The invention relates to a process for the preparation of perfluoroalkyl compounds using perfluoroalkyltrimethylsilanes of the general formula $(CH_3)_3Si-C_nF_{2n+1}$ (I), and to pentafluoroethyltrimethylsilane of the formula $(CH_3)_3Si-CF_2CF_3$, and to a process for the preparation of this compound.

Processes for perfluoroalkylation of carbonyl compounds are of great interest. Perfluoroalkyl metal compounds of non-noble metals, which are usually prepared from the corresponding perfluoroalkyl iodides and a metal such as Na, Li, Mg, Zn or Cd, are used for this purpose. The generally complex preparation and the lability of the perfluoroalkyl metal compound which must be prepared first are disadvantageous here, which is apparent from the fact, inter alia, that the published results can be reproduced only poorly. (Tetrahedron Letters 26, 5243–6 (1985), specially page 5245, footnote 4, and the references cited therein).

Further disadvantages are, for example, that the reaction must be carried out at low temperatures from $-78°$ C. to $-100°$ C. and at high dilutions (Tetrahedron Letters 26, 5243–6), that it is necessary to use ultrasound (Chem. Letters 1981, 1679–80), and that the process is limited to a few substrates, i.e. that only low yields, or none at all, are obtained on reaction of enolizable carbonyl compounds (J. Chem. Soc., Chem. Commun. 1987, 642–3).

The reaction of carbonyl compounds with pentafluorophenyltrimethylsilanes is known. However, the perfluoroaryl radical can only be transferred to the carbonyl compound on reaction with non-enolizable carbonyl compounds, such as benzaldehyde or trifluoroacetophenone; otherwise, the carbonyl compound is merely converted into the corresponding trimethylsilylenol ether, and transfer of the perfluoroaryl radical does not occur (J. Organometallic Chem. 292, 145–9 (1985); Chem. Letters 1972, 435–6).

Surprisingly, it has now been found that a perfluoroalkyl radical can be transferred from compounds other than organometallic compounds by reaction of perfluoroalkyltrimethylsilanes. It was particularly surprising that this reaction, in contrast to those described previously, give the perfluoroalkylation product desired even when enolisable carbonyl compounds are used.

The invention relates to a simple, one-step process for transfer of perfluoroalkyl radicals $C_nF_{2n+1}$ to carbonyl compounds by reaction thereof with perfluoroalkyltrimethylsilanes of the general formula $(CH_3)_3Si-C_nF_{2n+1}$ (I). In this process, silyl ethers of the general formula III (see Patent Claim 1) are formed in one step.

The process according to the invention has, in particular, the advantage of simplicity and of a great range of applications in the type and structure of the carbonyl compound employed. Thus, good yields of perfluoroalkylation products are achieved, even in cases where known processes give only low yields.

The simplicity of the process can be seen merely from the fact that it is sufficient to stir the two components for some time at room temperature in an inert solvent in the presence of a catalyst. In general, however, the reaction is carried out at 0° to 100° C., preferably at 20° to 60° C.. The reaction product can easily be isolated in the form of the silyl ether formed. The parent alcohols, which are known, can easily be obtained from these ethers by hydrolytic removal of the trimethylsilyl group.

Perfluoroalkyltrimethylsilanes which can be employed in the process according to the invention are those of the general formula $(CH_3)_3Si-C_nF_{2n+1}$ where $n=1$ to 6. n is preferably 1 to 4. The $C_nF_{2n+1}$ radicals can be straight-chain or branched.

The carbonyl compounds employed are compounds of the general formula $R^1-CO-R^2$ (II). The $R^1$ and $R^2$ radicals may have a wide variety of meanings. $R^1$ can denote any hydrocarbon radical, such as alkyl, alkenyl, cycloalkyl or aryl, or hydrogen; $R^2$ can likewise denote any hydrocarbon radical, such as alkyl, alkenyl, cycloalkyl or aryl, but also perfluoroalkyl or perfluoroaryl. $R^1$ and $R^2$ together may alternatively be part of an alicyclic ring system, i.e., together with the carbon atom of the carbonyl group, can denote, for example, the cyclopentylene or cyclohexylene radical, which may also be substituted by alkyl, such as methyl, ethyl or isopropyl. $R^1$ and $R^2$ each have, for example, 1 to 10, in particular, 1 to 6, carbon atoms. Suitable radicals are, for example, the methyl, ethyl, n- and isopropyl and the various butyl, pentyl, hexyl, octyl and decyl radicals, furthermore the vinyl or allyl radical, or the $C_6H_5CH=CH-$ radical and the phenyl or naphthyl radical, it being possible for the phenyl radical to be substituted by alkyl radicals having a total of up to 4 carbon atoms, i.e., for example, a tolyl, xylyl, cumyl, cymyl or t-butyl radical or a hydrogenation product thereof.

As the catalyst, salt-like fluorides are used which have a certain solubility in the reaction medium. Due to the ready accessibility, alkali fluorides and alkali bifluorides are preferred, the term alkali including ammonium bases. Potassium-fluorides and cesium fluoride are particularly suitable. In general, the catalyst is used in an amount of from 2 to 30 mol-%, preferably 10 to 25 mol-%, based on the carbonyl compound.

The present process is expediently carried under anhydrous conditions in the presence of a solvent or diluent which is inert to the reactants under the reaction conditions. Aprotic, polar solvents which have a certain solution capacity for the catalyst are suitable. Particularly suitable solvents are ethers, such as tetrahydrofuran or polyethers of the general formula $CH_3-O-[CH_2-Alk-O]_n-CH_3$ where $n=1$ to 4 and in which Alk denotes $CH-CH_3$ or preferably $CH_2$, and also dimethylformamide.

The process according to the invention can be carried out, for example, by initially introducing the solvent, carbonyl compound and catalyst and metering in the silane. The silane can be employed in an amount equivalent to the amount of the carbonyl compound or in excess, for example an excess of up to 25 mol-%. It is of advantage to ensure good mixing of the batch for the entire duration of the reaction, for example by stirring. The reaction is generally carried out at atmospheric pressure; however, it is also possible to carry out the reaction at increased or reduced pressure, even though this is generally not associated with any advantage.

The reaction mixture can be worked up by various methods. It is preferably worked up by distillative separation of the components. If, however, a water-soluble solvent such as tetraethylene glycol dimethyl ether is used, the reaction mixture can be worked up in a simple manner by extraction with water. The resultant, waterinsoluble crude product can then, if necessary, be purified by distillation.

The perfluoroalkyltrimethylsilanes are known in general terms. Only pentafluoroethyltrimethylsilane is novel and likewise subject-matter of the invention. The preparation succeeds in high yields by transfer of a perfluoroethyl group to chlorotrimethylsilane Cl—Si(CH$_3$)$_3$ in a manner different to the known preparation of trifluoromethyltrimethylsilane (Tetrahedron Letters 25, 2195-8)(1984)). Here, chlorotrimethylsilane is reacted with pentafluoroethyl iodide CF$_3$CF$_2$I and phosphorous acid trisdialkylamides (in other words tris(dialkylamino)phosphines) of the general formula P[N(alky)$_2$]$_3$, in general at temperatures between $-80°$ C. and 0° C., preferably between $-30°$ C. and $-10°$ C.. The known reaction of chlorotrimethylsilane takes place with trifluoromethyl bromide, more particular at "the lowest possible temperature" in methylene chloride or benzonitrile. Benzonitrile solidifies at only $-13°$ C. and, in addition, has an inadequate solution capacity at this temperature. Distillative separation of the methylene chloride from the lower perfluoroalkyltrimethylsilanes can only be carried out by expensive distillation. For this reason, one embodiment of the invention is carried out in the presence of polar, aprotic liquids which are inert to the reactants of the reaction conditions and whose boiling points are sufficiently different from those of the silanes to be prepared, for example at least 30° or, better, 40° C. higher. The use of n-butyronitrile, which is readily accessible industrially but still has good solution properties at low temperatures and whose boiling point is sufficiently different from that of pentafluoroethyltrimethylsilane, is particularly advantageous.

In general, the preparation of pentafluoroethyltrimethylsilane is carried out at atmospheric pressure, but can also be carried out at increased or reduced pressure, although this is generally not associated with any advantage. The preparation is expediently carried out under anhydrous conditions. It is of advantage to ensure good mixing of the batch for the entire duration of reaction, for example by stirring. The sequence of combining the three components is not critical. The preparation can be carried out, for example, by initially introducing the chlorotrimethylsilane and the pentafluoroethyl iodide and metering in the phosphorous acid trisdiethylamide. The two reagents are employed in an amount equivalent to the amount of chlorotrimethylsilane or in excess, for example an excess of 20 mol-%.

Suitable phosphorous acid trisdialkylamides (V) are, in particular, lower alkyl compounds, in particular those containing C$_1$-C$_4$-alkyl, such as trisdimethylaminophosphine, trisdiethylaminophosphine and trisdipropyl- or -isopropylaminophosphine; trisdiethylaminophosphine P[N(CH$_2$CH$_3$)2]3 is preferably used. This can be produced very simply in high yields by reacting phosphorus trichloride with diethylamine in a solvent which is inert towards the reaction, for example an aliphatic, cycloaliphatic or aromatic hydrocarbon or a hydrocarbon mixture. The dialkylamino groups can contain identical or different alkyl groups.

Since pentafluoroethyltrimethylsilane and the known perfluoroalkyltrimethylsilanes are thermally stable (up to 100° C.) and air- and moisture-stable compounds, they can be handled very simply for further reactions, in contrast to many other perfluoroorganometallic compounds.

EXAMPLES (1) 43.5 g (0.4 mol) of chlorotrimethylsilane were introduced into 100 ml of butyronitrile in a round-bottom flask with exclusion of moisture at about $-20°$ C.. 110 g (0.45 mol) of penta-fluoroethyl iodide were condensed in, and 100.8 g (0.4 mol) of phosphorous acid trisdiethylamide were then metered in over the course of 45 minutes at $-25°$ C. to $-20°$ C. The reaction mixture was subsequently kept at about $-15°$ C. to $-10°$ C. for 5 hours with thorough stirring and then slowly warmed to room temperature. The silane produced was condensed into a cold trap at about 50 mbar.

Redistillation of the crude product (79 g) gave 66.7 g (87% yield) of pentafluoroethyltrimethylsilane of boiling point 69-71° C./ 1013 mbar C$_5$H$_9$F$_5$Si Calc.: C 31.24 H 4.68 F 49.42
192.21 Found: C 31.4 H 4.8 F 49.3
$^{19}$F NMR (CDCl$_3$): $-82.5$ (3F,CF$_3$); $-131.8$ (2F,CF$_2$)

(2) 12 g (0.1 mol) of acetophenone were introduced into 50 ml of tetraethylene glycol dimethyl ether in a round-bottom flask equipped with reflux condenser, internal thermometer and a means of external cooling. After 1 g of potassium fluoride had been added, 20.2 g (0.105 mol) of pentafluoroethyltrimethylsilane were added dropwise with thorough stirring. The reaction mixture was kept at between 20° and 30° C. After 6 hours, the ketone had reacted according to IR spectroscopy. Distillation of the reaction mixture gave 26.4 g (85% yield) of silyl ether of boiling point 78°-79° C./5 mbar.

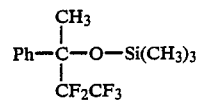

Calc.: C 49.99 H. 5.49 F 30.41
Found: C 50.1 H 5.5 F 30.2
$^{19}$F NMR (CDCl$_3$): $-78.1$ (3F,CF$_3$); $-125.5$ (2F,CF$_2$)
$^1$H NMR (CDCl$_3$): 1.92 (s,3H,CH$_3$); 7.3-7.7 (m,5H,aromatic); 0.2 (s,9H, CH$_3$—Si)

(3) 5.8 g (0.1 mol) of acetone and 14.2 g (0.1 mol) of trifluoromethyltrimethylsilane were introduced in 50 ml of tetraethylene glycol dimethyl ether in the apparatus described in Example 2. After 1 g of KF had been added, the reaction mixture warmed spontaneously. When the exothermic reaction was complete, the reaction mixture was distilled, and 14.6 g (73% yield) of silyl ether of boiling point 104°-105° C./1013 mbar were obtained.

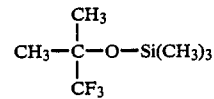

Calc.: C 41.98 H 7.55 F 28.46
Found: C 41.8 H 7.4 F 28.2
$^{19}$F NMR (CDCl$_3$): $-84.7$ (3F,CF$_3$)
$^1$H NMR (CDCl$_3$): 1.22 (m,6H,CH$_3$); 0.1 (s,9H,CH$_3$—Si)

(4) 10 g (0.1 mol) of methyl isobutyl ketone and 1 g of potassium fluoride were introduced into 50 ml of tetraethylene glycol dimethyl ether in the apparatus described in Example 2. 21.2 g (0.11 mol) of pentafluoroethyltrimethylsilane were added dropwise at 20° to 30° C. with thorough stirring. After 18 hours, 50 ml of hexane were added dropwise; the reaction mixture was extracted twice with 100 ml of water, and the resultant organic phase was dried over Na₂SO₄. On distillation, 21.9 g (75% yield) of silyl ether of boiling point 93°–94° C./52 mbar were obtained.

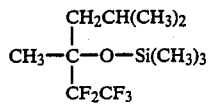

Calc C 45.19 H 7.24 F 32.49
Found: C 45.3 H 7.1 F 32.2
¹⁹F NMR (CDCl₃): −78.2 (3F,CF₃); −123.3 (2F,CF₂)
¹H NMR (CDCl₃): 0.83 (m,6H, CH₃—CH); 1.29 (s,3H,CH₃); 1.43 (m,2H,CH₂); 1.6–1.9 (m,1H,CH); 0.1 (s,9H, CH₃—Si).

(5) On reaction of 8.4 g (0.1 mol) of cyclopentanone with 21.2 g (0.11 mol) of pentafluoroethyltrimethylsilane analogously to the process described in Example 4, 18.2 g (66% yield) of silyl ether of boiling point 88°–89° C./52 mbar were obtained.

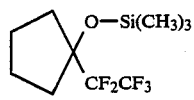

Calc.: C 43.66 H 6.2 F 34.38
Found: C 43.3 H 6.1 F 34.5
¹⁹F NMR (CDCl₃): −79.4 (3F,CF₃); −122.9 (2F,CF₂)
¹H NMR (CDCl₃): 1.6 (m,4H,CH₂); 1.8 (m,4H,CH₂); 0.1 (s,9H, CH₃—Si).

(6) On reaction of 18.2 g (0.1 mol) of benzophenone with 15.6 g (0.11 mol) of trifluoromethyltrimethylsilane in 80 ml of tetraethylene glycol dimethyl ether analogously to the process described in Example 4, 26.2 g (81% yield) of silyl ether of boiling point 98°–99° C./0.3 mbar (m.p.: 28°–30° C.) were obtained.

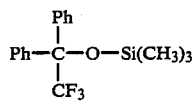

Calc.: C 62.94 H 5.9 F 17.57
Found: C 63.2 H 5.9 F 17.3
¹⁹F NMR (CDCl₃): −73.1 (3F,CF₃)
¹H NMR (CDCl₃): 7.3–7.6 (m,10H,aromatic); 0.1 (s,9H,CH₃—Si).

(7) On reaction of 16.2 g (0.1 mol) of trifluoroacetophenone with 21.2 g (0.11 mol) of pentafluoroethyltrimethylsilane analogously to the process described in Example 4, 26.4 g (85% yield) of silyl ether of boiling point 89° C./18 mbar were obtained.

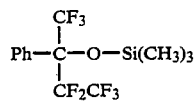

Calc.: C 44.06 H 3.98 F 42.9
Found: C 44.3 H 3.8 F 42.3

¹⁹F NMR (CDCl₃): −70.3 ((t,3F,CF₃); −78.5 (m,3F,CF₃CF₂); −119.5 (m,2F,CF₂)
¹H NMR (CDCl₃): 7.4–7.7 (m,5H, aromatic); 0.2 (s,9H, CH₃—Si).

(8) On reaction of 5.6 g (0.1 mol) of acrolein with 15.6 g (0.11 mol) of trifluoromethyltrimethylsilane analogously to the process as described in Example 4, 14.8 g (75% yield) of silyl ether of boiling point 53°–54° C./100 mbar were obtained.

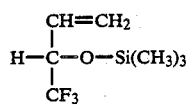

Calc.: C 42.4 H 6.61 F 28.75
Found: C 42.5 H 6.8 F 29.1
¹⁹F NMR (CDCl₃): −79.52 (d,3F,CF₃)
¹H NMR (CDCl₃): 4.46 (m,1H, CH—CH₃); 5.4–6.2 (m,3H) CH=CH₂) 0.1 (s,9H, CH₃—Si).

(9) On reaction of 10.6 g (0.1 mol) of benzaldehyde with 26.6 g (0.11 mol) of heptafluoroisopropyltrimethylsilane analogously to the process as described in Example 4, 23.3 g (67% yield) of silyl ether of boiling point 107°–109° C./35 mbar were obtained.

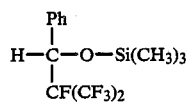

Calc.: C 44.82 H 4.34 F 38.18
Found: C 44.6 H 4.3 F 38.4
¹⁹F NMR (CDCl₃): −72.9 (m,F,CF₃); −180.3 (m,1F,CF)
¹H NMR (CDCl₃) 5.2 (m,1H,CH); 7.2–7.5 (m,5H, aromatic); 0.1 (s,9H,CH₃—Si).

(10) 10.6 g (0.1 mol) of benzaldehyde and 1 g of potassium fluoride were introduced into 50 ml of tetraethylene glycol dimethyl ether in a round-bottom flask. 15.6 g (0.11 mol) of trifluoromethyltrimethylsilane were added dropwise at 20° C. to 30° C. with thorough stirring. After a further 5 hours at this temperature, the mixture was worked up analogously to Example 4. On the distillation of the crude product, 23.3 g (90% yield) of silyl ether of boiling point 63°–64° C./6 mbar were obtained.

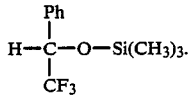

Calc.: C 53.2 H 6.09 F 22.96
Found: C 53.3 H 6.1 F 22.8 ¹⁹F NMR (CDCl₃): −78.6 (d, J=6Hz (F—H), 3F, CF₃)
¹H NMR (CDCl₃): 4.81 (q, J=6Hz, (H—CF₃), 1H, CH), 7.2–7.4 (m,5H, aromatic); 0.1 (s,9H, CH₃—Si).

(11) Benzaldehyde was reacted with trifluoromethyltrimethylsilane as in Example 10. After a reaction time of 5 hours, 20 ml of water were added, and the reaction mixture was heated briefly to 80° C. 50 ml of hexane were then added. The reaction mixture was then extracted twice with 100 ml of water, and the resultant organic phase was dried over Na₂SO₄. On distillation of the crude product, 15.4 g (88% yield) of 1-phenyl-2,2,2- trifluoroethanol (boiling point 68°-69° C./6 mbar) were obtained.

We claim:

1. A process for the preparation of perfluoroalkyl compounds which comprises reacting a perfluoroalkyltrimethylsilane of the general formula $(CH_3)_3Si-C_nF_{2n+1}$ (I), wherein the group $C_nF_{2n+a}$ represents a perfluoroalkyl group having from 1 to 6 carbon atoms, with a carbonyl compound of the general formula $R^1-CO-R^2$ (II), wherein $R^1$ represents a hydrocarbon group or hydrogen and $R^2$ represents a hydrocarbon group, a perfluoroalkyl group or a perfluoroaryl group, but wherein $R^1$ and $R^2$ together may also be part of an alicyclic ring system, in the presence of a fluoride salt—which is at least partially soluble in the reaction medium—as a catalyst to yield a silylether of the formula

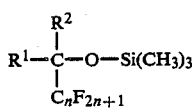

and isolating this compound of hydrolyzing it to yield an alcohol of the formula IV

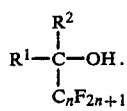

2. A process as claimed in claim 1, wherein the fluoride is an alkali fluoride or alkali bifluoride.

3. A process as claimed in claim 2, wherein the fluoride is potassium fluoride or cesium fluoride.

4. A process as claimed in claim 1, wherein the catalyst is applied in an amount of from 2 to 30 mol-%, referred to the carbonyl compound II.

5. A process as claimed in claim 4, wherein the catalyst is applied in an amount of from 10 to 25 mol-%, referred to the carbonyl compound II.

6. A process as claimed in claim 1, which is carried out under anyhydrous conditions in the presence of a solvent or diluent which under the reaction conditions is inert towards the reactants and has a solvent capacity for the catalyst.

7. A process as claimed in claim 1, which is carried out at a temperature in the range of from 0° to 100° C.

8. A process as claimed in claim 7, which is carried out at a temperature in the range of from 20° to 60° C.

9. A process as claimed in claim 1, wherein the silane I is applied in an amount at least equivalent to the carbonyl compound and at most in an amount up to 25 mol-% above the equivalent amount.

10. A process as claimed in claim 1, wherein $R^1$ and $R^2$ in the carbonyl compound II each have from 1 to 10 carbon atoms.

11. A process as claimed in claim 1, wherein $R^1$ and $R^2$ in the carbonyl compound II each have from 1 to 6 carbon atoms.

12. A process as claimed in claim 6, wherein the solvent is an ether selected from the group consisting of tetrahydrofuran and a polyester of the formula $CH_3-O-[CH_2-alk-O]_n-CH_3$ wherein n is an integer from 1 to 4 and alk represents $CH-CH_3$ or $CH_2$.

13. A process as claimed in claim 6, wherein the solvent is dimethylflormamide.

* * * * *